United States Patent [19]

Gong et al.

[11] Patent Number: 4,490,468
[45] Date of Patent: Dec. 25, 1984

[54] PRODUCTION OF ETHANOL BY YEAST USING XYLULOSE

[75] Inventors: Cheng Shung Gong; Li Fu Chen, both of West Lafayette; Michael C. Flickinger, Battle Ground; George T. Tsao, West Lafayette, all of Ind.

[73] Assignee: Purdue Research Foundation, W. Lafayette, Ind.

[21] Appl. No.: 143,146

[22] Filed: Apr. 23, 1980

[51] Int. Cl.$^3$ ................................................ C12P 7/06
[52] U.S. Cl. ............................. 435/161; 435/163; 435/162; 435/921; 435/930; 435/938; 435/940
[58] Field of Search ................ 435/94, 927, 161, 930, 435/162, 938, 163, 940, 105, 172, 255, 256, 813, 234

[56] References Cited

U.S. PATENT DOCUMENTS

| | | | |
|---|---|---|---|
| 2,481,263 | 9/1949 | Tsuchiya et al. | 435/161 X |
| 2,950,228 | 8/1960 | Marshall | 435/94 |
| 3,813,318 | 5/1974 | Armbruster et al. | 435/233 X |
| 3,957,587 | 5/1976 | Armbruster et al. | 435/234 |
| 3,992,262 | 11/1976 | Shieh | 435/234 |

OTHER PUBLICATIONS

Schneider et al., Bioenergy'80 Abstracts "Fermentation of a Pentose by Yeasts" Apr. 22, 1980 pp. 68 & 71.
Schneider et al. Bioenergy'80 Proceedings "Fermentation of a Pentose by Yeasts" Apr. 22, 1980 pp. 573-574.
Karczewska "Some Observations on Pentose Ultilization by Candida & Ropicalcs" Compt. Rend. Lab Carlsberg vol. 31 No. 17 (1959) pp. 251-258.
Plevaks et al. "Biologic Observations on Yeasts Utilizing Pentoses" Microbiologya (1935) vol. 4 pp. 86-94.
Tomoyeda et al., "Pentose Metabolism by Candida Utilis" Part I Glucose Isomerase" Ag. Bid. Chem. vol. 28 pp. 139-143 (1964).
Wang et al. Fermentation of D-xylose by Yeasts Using Glucose Isomerase in the Medium to Convert D-xylose to D-xylulose Chem. Abst. 93:130538n (1980).
Sitton et al., "Ethanol from Agricultural Residues" Chemical Abstracts vol. 92 (1980) Abstract No. 74333g.
Stankovie et al., "Isomenzation of Penlases & 2-Penlulases by Inorganic Phosphates" Ca vol. 92 (1980) Abstract No. 18367j.
Suresh "Acid Catalyzed interconversion of xylose, xylulased lyxose Chemical Abstracts vol. 91 (1979) Abst. No. 5423d.
Sankernarayam et al. "Fermentative conversion of xylose into chemicals" Chem. Abst. vol. 93 (1980) Abst. No. 24419q.

*Primary Examiner*—R. B. Penland
*Attorney, Agent, or Firm*—Cushman, Darby & Cushman

[57] ABSTRACT

Ethanol is produced by the fermentation of xylulose using yeast under fermentative conditions.

9 Claims, 3 Drawing Figures

PRODUCTION OF ETHANOL BY YEAST USING XYLULOSE

BACKGROUND OF THE INVENTION

The present invention relates to a biological conversion of xylulose to ethanol by fermenting xylulose with a yeast under fermentative conditions. Fermentative conditions are generally recognized to be the conditions largely anaerobic, but sometimes with limited oxygen supply, and which are suitable for producing ethanol.

With petroleum resources dwindling throughout the world, efforts are being made to utilize alternative sources of energy. Recently, mixtures of gasoline and alcohol have been touted as but one means of alternate energy savings. In order to provide sufficient gasohol products, an economic means for producing the necessary alcohol is needed. Heretofore, production of such alcohol has been chiefly carried out by the conversion of six-carbon sugars derived mainly from grain products and cane sugar juice or molasses. With the increase in value of such six-carbon sugar materials, there is a need for alternative economic feedstocks for the production of alcohol. Much of the available hemicellulosic feedstock which has been regarded as waste products, such as bagasse, remain untapped due to the lack of a viable economic means to convert such hemicellulosic waste materials to useful energy forms such as ethanol.

Numerous methods are known for producing small amounts of ethanol from six-carbon sugars under submerged cultural conditions using mycelial fungi as illustrated for example in U.S. Pat. Nos. 3,936,353; 3,591,454; 2,556,084; 1,572,539; 1,472,344, and 1,266,657. These methods however, do not provide a means for the conversion of five-carbon monosaccharides such as xylose and xylulose to ethanol.

Many yeasts are capable of fermenting hexoses to ethanol anaerobically with high yields. However, no yeasts have been reported to ferment pentoses to ethanol, even though many yeasts are capable of metabolizing pentoses aerobically. Therefore, the pentoses which are derived primarily from hemicellulosic materials have been reported to be nonfermentable sugars. Several bacteria (e.g., *Clostridia*) and mycelial fungi (e.g., *Mucor* spp., *Rhizopus* spp., and *Fusaria*) are known to metabolize as well as ferment pentoses to ethanol. For ethanol production from biomass, yeasts are preferred over bacteria and mycelial fungi. The yeast process for fermenting glucose to ethanol is a relatively simple well-studied process. *Clostridia* fermentation of pentoses are not satisfactory due to the low yield and generating organic acid (e.g., acetic acid) as fermentation products along with ethanol. See for example U.S. Pat. No. 1,857,429.

The biological conversion of five-carbon sugars derived from hemicellulose to ethanol is important to fully utilize biomass to produce liquid fuels, especially in view of the fact that vast quantities of hemicellulosic materials are readily available, but under-utilized due to the lack of the ability of proper organisms to convert pentoses to ethanol efficienty. The research into possible large-scale utilization of hemicellulose derived sugars as substrates to convert it to ethanol has thus received little attention. One major reason for this inadequacy is that the fundamental knowledge concerning the metabolism of pentoses by microorganisms and converting it into ethanol is insufficient.

The utilization and conversion of pentoses into ethanol requires the involvement of enzymes which are not required for D-glucose fermentation.

It is a primary object of the present invention to provide a new technique for the production of ethanol from xylose and xylulose materials.

It is a further object of the present invention to provide a means for production of ethanol from xylose and xylulose which is compatible with conversion of six-carbon sugars.

These and other objects will be more apparent from the discussion below.

SUMMARY OF THE INVENTION

The present invention provides for the production of ethanol by fermenting xylulose under fermentative conditions in the presence of a yeast.

As used herein the term fermentative conditions is defined as conditions which are largely anaerobic, but sometimes with limited oxygen supply (i.e., in contrast to aerobic conditions) suitable for producing ethanol.

By addition of isomerized xylose into the fermentation medium followed by analysis of xylulose disappearance and ethanol production, we have found that yeasts e.g., *Saccaromyces* spp., *Candida* spp., and *Torula* spp.) are able to convert xylulose to ethanol readily. These observations clearly indicate that the limiting factor for ethanol production from xylose by yeasts is due to the deficiency of isomerizing enzyme of yeasts. In order to ferment pentoses to ethanol, the barrier for xylose isomerization must be overcome.

Several yeasts belonging to the genus *Rhodotorula* and *Rhodosporidium* are known to produce xylose isomerase in a growth medium which contains xylose; however, they are not able to ferment pentoses to ethanol.

DETAILED DESCRIPTION OF THE INVENTION

The fermentation of xylulose to ethanol may be accomplished using a wide variety of conditions and materials. The fermentation reaction may be carried out batchwise or continuously.

Xylulose heretofore has found little use, but has been reported for the preparation of xylitol under aerobic conditions as set forth in U.S. Pat. No. 3,619,369. Xylulose may be obtained commercially, but due to the relatively high cost, it is generally desirable to obtain the material by alternative sources. Thus, one may obtain xylulose by isomerization of xylose using glucose isomerase or xylose isomerase. Chemical isomerization of xylose is also a suitable means of obtaining xylulose. Another means of obtaining xylulose is by biological conversion of xylose, glucose or other sugars such as arabitol and xylitol.

In accordance with the present invention, we have found that while yeast cannot utilize xylose to produce ethanol, yeast can utilize xylulose for ethanol production. Thus, in accordance with the present invention, one can combine *in vitro* and *in vivo* isomerization processes together with fermentation processes with yeast to produce ethanol from xylose, which of course is a major product of the acid hydrolysis of hemicellulose from various sources of biomass.

As a result of the present invention, one can accomplish fermentation of, for example glucose and xylose, using the same organism - yeast. Such a possibility may reduce the cost of ethanol production considerably.

As noted above, the process parameters may vary widely. As used herein, the term yeast refers to those yeasts capable of fermenting xylulose to ethanol under fermentative conditions as defined above. Exemplary (but not limited to) of such yeasts include those of the genus *Saccharomyces, Candida, Torula, Schizosaccharomyces, Pichia,* and *Hansenula.* Of these, the genus *Saccharomyces* is preferred.

The fermentation of xylulose should be carried out anaerobically at a temperature ranging from about 5° C. to 45° C., and preferably within the range of about 24° C. to 35° C., ambient temperature being particularly suitable.

Fermentation can be carried out at a pH ranging from 3.0 to 9.0 but is preferably within the range of 4.0 to 6.0.

In many instances it may be desirable to carry out the production of xylulose and fermentation thereof in a stepwise or simultaneous manner using the procedure of:

(a) isomerizing xylose to form xylulose; and
(b) fermenting the xylulose to produce ethanol.

BRIEF DESCRIPTION OF THE DRAWINGS

The production of ethanol according to the present invention may be carried out in either a batchwise or continuous manner.

Figure 1:
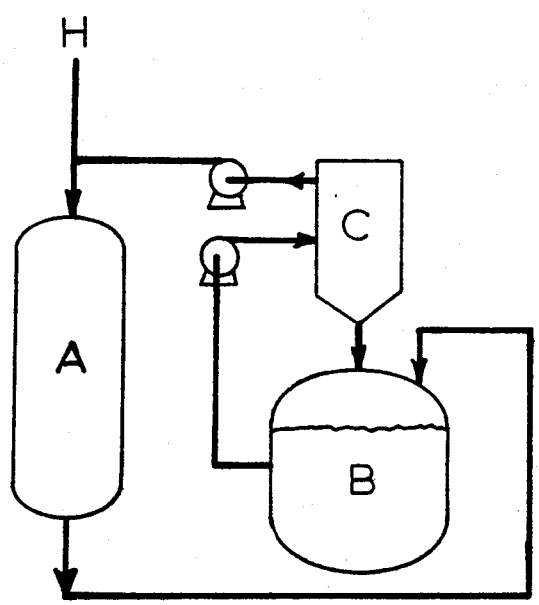
FIG. 1 is a schematic diagram for batch production of ethanol.

With specific reference to FIG. 1, the batch processing for ethanol production is carried out by introducing a xylose containing material H into an isomerization reactor A which may contain whole cells, (e.g., *Actinoplanes*) which contain xylose isomerizing enzymes, or xylose isomerizing enzymes (soluble or immobilized). The resulting xylulose containing material (initial fermentation substrate) after appropriate adjustment of pH and/or temperature if needed, is then fed to a fermentor vessel B containing the required fermentation yeast. After a sufficient period for fermentation, the mixture is pumped to a cell separator C (i.e., settler or centrifuge) wherein the yeast cells and other insolubles are separated and returned to the fermentor B. The resulting liquid which contains xylose which was not isomerized in its earlier passage through the isomerization reactor A is recycled to the reactor A. Once all the xylose in the original material H has been isomerized to xylulose which in turn has been converted to ethanol, the system is drained, possibly retaining the insolubles for recycle if desired, and the remaining reaction mixture is distilled for separation of alcohol (not depicted).

Figure 2:
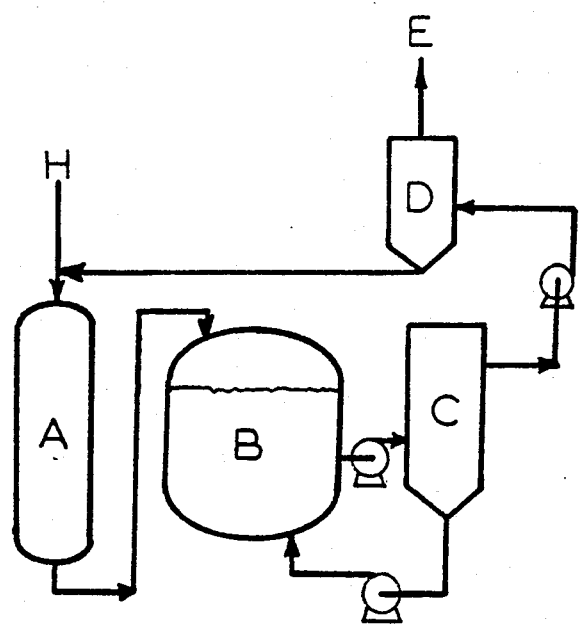
FIG. 2 is a schematic diagram for continuous ethanol production.

For the continuous process of ethanol separation, reference is made to FIG. 2 wherein a xylose containing material H is fed into an isomerization reactor A which may contain whole cells (e.g., *Actinoplanes*) containing xylose isomerizing enzymes or xylose isomerizing enzymes (soluble or immobilized). The resulting xylulose containing material (i.e., initial fermentation substrate), after any desired adjustment in pH and/or temperature, is passed to the fermentor vessel B which contains the required yeast. After fermentation of the substrate, the mixture is pumped to a cell separator C (i.e., a settler or centrifuge) wherein the yeast cells and insoluble materials are separated and pumped back to the fermentor vessel B. The remaining liquid is pumped to a vacuum evaporator D wherein a mixture of ethanol and water E is separated from the xylose containing material for further processing if desired (i.e., distillation, etc.). The remaining xylose material is returned to the reactor A for further isomerization to xylulose.

The following examples are offered in an effort to more fully illustrate the invention, but are not to be construed as limiting the scope thereof.

EXAMPLE ONE

Xylose (100 gm) was dissolved in distilled water to provide a concentration of 60% w/v. The solution was placed in a reaction vessel to which was added $CoCl_2$ and $MgCl_2$ to provide a concentration of $Co^{++} = 10^{-4}M$ and $Mg^{++} = 10^{-3}M$. The pH of the solution was adjusted to 7.5 by the addition of a phosphate buffer. To the resulting solution was then added 5 gm of glucose isomerase extracted from *Streptomyces* and the temperature was maintained at 60° C. overnight (18 hours). The solution was then added to a fermentation medium (DIFCO 8.5 gm/l yeast extract, $NH_4Cl$ 1.3 gm/l, $MgSO_4 \cdot 7 H_2O$ 0.11 gm/l, and $CaCl_2$ .06 gm/l) to yield an initial fermentation substrate concentration of 78 gm/l xylose and 20 gm/l xylulose. The resulting pH was 5.5.

Figure 3:
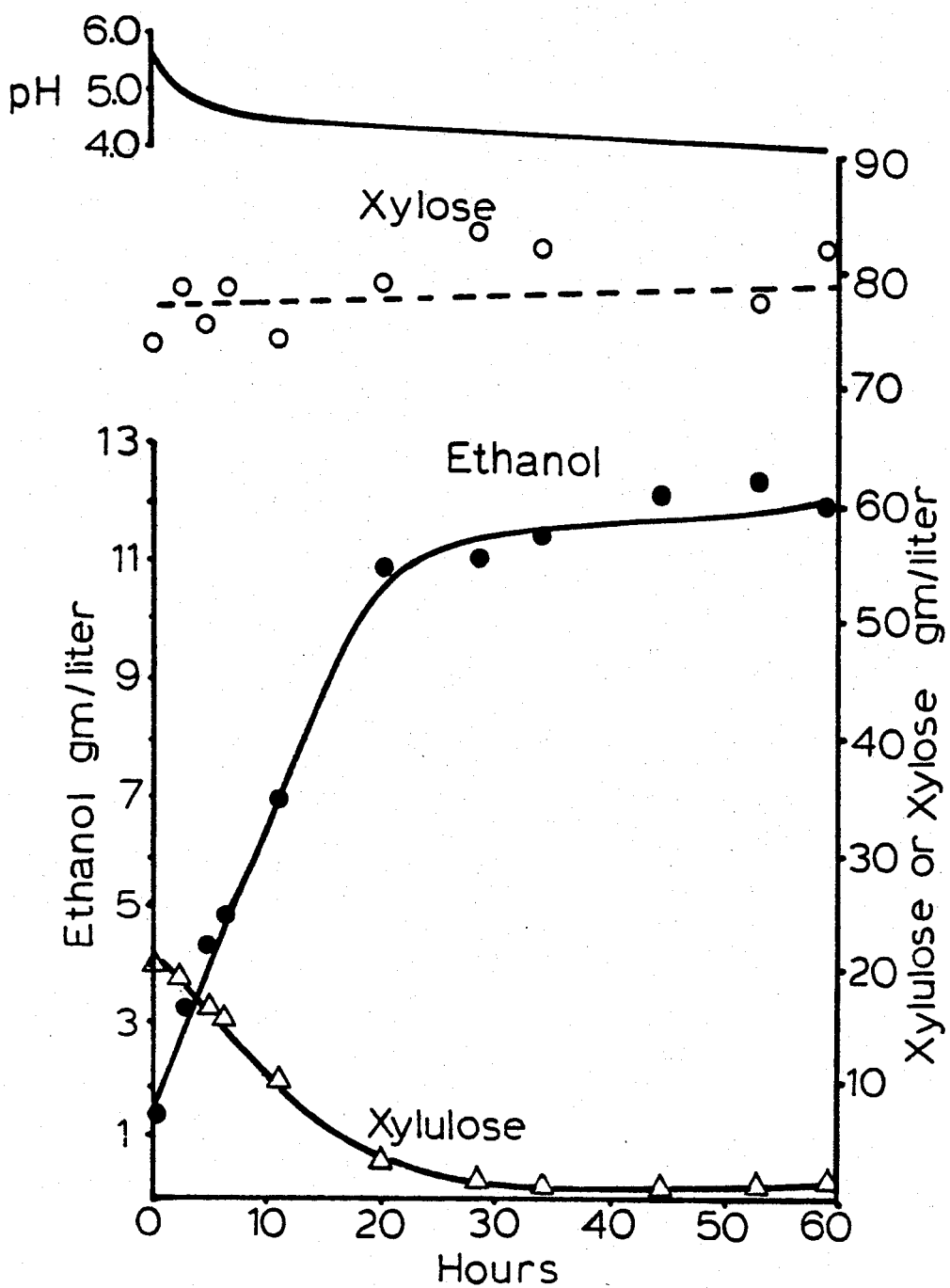
FIG. 3 is a graph illustrating growth, xylulose uptake and ethanol production by *Saccharomyces cerevisiae.*

To the initial substrate maintained at ambient temperature (about 24° C.) was then added 45 gms of commercial yeast cake (*Saccharomyces*). The reaction vessel was covered and continuously agitated and maintained at ambient temperature to allow fermentation to proceed. Reaction samples were periodically removed and analyzed to determine the ethanol, xylose, and xylulose concentrations over a period of 60 hours and the results are depicted in FIG. 3.

EXAMPLE TWO

The procedure of Example One was repeated to produce an initial substrate except that the pH was adjusted by the addition of KOH to provide a pH of 7.0 and an initial fermentation substrate concentration of 52 gm/l. xylose and 14 gm/l xylulose, which was then fermented with a commercial yeast cake (*Saccharomyces*). The reaction produced a maximum ethanol production level of 5.3 gm/l (yield = 81% of theoretical conversion of xylulose).

EXAMPLE THREE

Xylose was dissolved in distilled water at a concentration of 80 gm/l together with 25 gm of wet cell *Actinoplanes* (an isomerization enzyme containing bacteria). The pH was adjusted to 7.0 by addition of a phosphate buffer. The temperature of the reaction mixture was maintained at ambient temperature (about 24° C.) and 45 gms of commercial yeast cake (*Saccharomyces*) per liter of fermentation broth was added and the fermentation was allowed to proceed for a period of 60 hours during which the amount of ethanol formed was monitored. Results showed the maximum level of ethanol produced was 5.6 gm/l to give a theoretical yield of 33% based on the conversion of xylose.

EXAMPLE FOUR

The procedure of Example Two was repeated to provide an initial fermentation substrate containing 59 gm/l xylose and 16.5 gm/l xylulose.

As in Example Two, yeast cake was added to the substrate at a pH of 7.0 and ambient temperature and fermentation allowed to proceed. The maximum level of ethanol produced was 6.1 gm/l with a yield of 88% based on xylulose conversion.

EXAMPLE FIVE

Upon reaching a maximum conversion level of xylulose to ethanol in the fermentation of Example Four, 25 gms of wet *Actinoplanes* cells were added to the fermentation mixture, so as to facilitate isomerization of remaining xylose to xylulose, and subsequent fermentation of xylulose to ethanol. The yield of ethanol based on xylulose so isomerized was 80% of theoretical.

EXAMPLE SIX

Sixty grams of xylose was dissolved in distilled water to form a 0.4 molar solution to which was added 174 gms sodium aluminate (0.8 molar). Isomerization was carried out at ambient temperature for seventy (70) hours. Thereafter, phosphoric acid was added to adjust the pH to 6.0 to precipitate aluminum phosphate. The mixture was then centrifuged and filtered. The supernatant was passed through a mixed bed ion exchange column (cation/anion) to remove residual salt.

The resulting solution was evaporated to form an initial fermentation substrate solution having 88 gm/l xylulose and 22 gm/l xylose.

The initial fermentation substrate solution was then fermented using a variety of yeasts. In each instance, fermentation was carried out at a temperature of 30° C. and an initial pH of 5.5 for 20 hours. The amount of ethanol produced was monitored and the results are set forth in Table 1 below.

TABLE 1

ETHANOL OBTAINED FROM CHEMICALLY ISOMERIZED XYLULOSE

| | FERMENTATION YEAST | PERCENTAGE OF ETHANOL PRODUCED (Wgt/Volume) |
|---|---|---|
| Run 1 | *Saccharomyces cerevisiae* | 2.1 |
| Run 2 | *Saccharomyces diastaticus* | 1.57 |
| Run 3 | *Candida sp.* | 2.63 |
| Run 4 | *Candida utilis* | 2.40 |
| Run 5 | *Torula sp.* | 2.64 |

While not wishing to be limited to the following observations and explanations, it appears that the yield of ethanol from xylulose is at its maximum (100% conversion) when the pH of the fermentation is allowed to fall to about 4.0.

In some instances it may be desirous to carry out simultaneous isomerization and fermentation in which instance the pH of the reaction mixture is preferably about 7.0 (e.g., 6.8 to 8.0).

The highest yield, conversion rate and final ethanol concentration from xylose occurs under the following fermentation conditions:

(A) Pre-isomerized xylose to xylulose; and
(B) Fermentation pH down to pH 4.0 with minimal agitation.

With the above conditions, the yield of ethanol from xylulose is essentially quantitative without xylitol formation.

It will be apparent to those knowledgeable in the art of genetic engineering that in view of the fact that the limiting factor for ethanol production from xylose by yeasts described above, various modifications could be made to yeasts to overcome the deficiency of yeasts for isomerization of xylose. For example, one may employ a variety of known techniques to modify the isomerization capacity of yeasts, including but not limited to DNA-recombination, protoplasts fusion and genetic mutation.

The invention having been thus described, it is understood that various modifications can be made thereto without departure from the scope thereof. Furthermore, the invention may comprise, consist or consist essentially of the hereinbefore state materials and steps.

What is claimed is:

1. A process for the production of ethanol which comprises fermenting xylulose under fermentative conditions at a pH ranging from 3.0 to 9.0 and a temperature ranging from about 5° to 45° C. with a yeast selected from the genus consisting of *Saccharomyces, Candida, Torula, Schizosaccharomyces, Pichia* and *Hensenula*.

2. A process according to claim 1 wherein said yeast is from the genus Saccharomyces.

3. A process according to claim 1 wherein said pH is from about 4.0 to 6.0.

4. A process according to claim 1 wherein the temperature ranges from about 24° to 35° C.

5. A process according to claim 1 wherein said xylulose is obtained by isomerization of xylose.

6. A process according to claim 5 wherein isomerization and fermentation are carried out simultaneously.

7. A process for the production of ethanol from xylose which comprises the steps of:
(a) isomerizing xylose to form xylulose; and
(b) fermenting said xylulose according to the process of claim 1 whereby ethanol is produced.

8. A process according to claim 7 where step (a) is carried out in the presence of glucose isomerase or xylose isomerase.

9. A process according to claim 5 wherein steps (a) and (b) are carried out simultaneously.

* * * * *